United States Patent
Wang (10) Patent No.: US 11,529,245 B2
(45) Date of Patent: Dec. 20, 2022

(54) KINEMATIC-AXIS LOCATING DEVICE FOR KNEE ARTHROPLASTY

(71) Applicant: Chih-Chien Wang, Tainan (TW)

(72) Inventor: Chih-Chien Wang, Tainan (TW)

( * ) Notice: Subject to any disclaimer, the term of this patent is extended or adjusted under 35 U.S.C. 154(b) by 275 days.

(21) Appl. No.: 17/036,595

(22) Filed: Sep. 29, 2020

(65) Prior Publication Data

US 2022/0096247 A1    Mar. 31, 2022

(51) Int. Cl.
    *A61B 17/15*      (2006.01)
    *A61F 2/46*       (2006.01)
    *A61F 2/30*       (2006.01)

(52) U.S. Cl.
CPC ............ *A61F 2/4657* (2013.01); *A61F 2/461* (2013.01); *A61F 2002/30754* (2013.01); *A61F 2002/4668* (2013.01)

(58) Field of Classification Search
CPC .............. A61B 17/157; A61B 17/1764; A61B 2017/0268; A61F 2/4657
See application file for complete search history.

(56) References Cited

U.S. PATENT DOCUMENTS

| | | | |
|---|---|---|---|
| 8,900,242 B2 | 12/2014 | Murray et al. | |
| 2013/0331850 A1* | 12/2013 | Bojarski | A61F 2/4657 606/102 |
| 2017/0333018 A1* | 11/2017 | Sehat | A61B 17/1764 |

* cited by examiner

*Primary Examiner* — Samuel S Hanna
(74) *Attorney, Agent, or Firm* — Muncy, Geissler, Olds & Lowe, P.C.

(57) ABSTRACT

A kinematic-axis locating device for knee arthroplasty includes two spoon-shaped arms and a linking piece. The two spoon-shaped arms are to be placed between a proximal tibia and a distal femur. Due to checking effects of ligaments on the proximal tibia and the distal femur, a medial condyle femur and a lateral condyle femur hold the two spoon-shaped arms on the tibial plateau using their respective curvatures. The linking piece provides a reference axis that is naturally defined by the two inserted and positioned spoon-shaped arms. The reference axis is roughly parallel to a kinematic axis upon which the medial condyle and the lateral condyle pivot against the tibial plateau. Articular surface resection can then be performed between the proximal tibia and the distal femur with reference to the reference axis.

8 Claims, 8 Drawing Sheets

KINEMATIC-AXIS LOCATING DEVICE FOR KNEE ARTHROPLASTY

BACKGROUND OF THE INVENTION

1. Field of the Invention

The present invention relates to devices used in knee arthroplasty, and more particularly to a kinematic-axis locating device for knee arthroplasty.

2. Description of the Related Art

Among the various joints in a human body, knee joints at lower limbs are ones of the most burdened and most frequently rubbed. As people get old, their knee joints can unavoidably have abrasion, which is usually accompanied by pains. Serious abrasion will eventually make the patients have difficulty in walking and inconvenience their daily life. In this case, a surgical operation for implanting a prosthetic joint may be required as a treatment.

Total knee arthroplasty (TKA) is a known operation. It involves resection the patient's proximal tibia and distal femur, and then implanting a prosthetic joint and a spacer. Therein, resection made on the proximal tibia and the distal femur is irreversible, and forms a crucial factor in whether the prosthetic joint can be well adapted the patient's primordial bones, making this process a key challenge for knee arthroplasty.

One conventional approach to the foregoing resection is mechanical alignment (MA), which uses a link between center of rotation of the femur and the midpoint between medial/lateral condyle through the center of the proximal tibia as a reference axis. This mechanical axis can generally be obtained using fluoroscopy. For implantation of a prosthetic, both the proximal tibia and the distal femur are first cut to provide articular surfaces perpendicular to the mechanical axis, then the prosthetic joint and the spacer can be arranged between the cuts.

However, as clinically observed through, for example, demographic data, there are only less than 2% of the total population having lower limbs that meet the setting of the foregoing mechanical axis. If fact, genu varum and genu valgum of varying degrees are not rare among patients. With either deformity, the articular surfaces of a patient's proximal tibia and distal femur are not perpendicular to the mechanical axis.

While an MA-based operation can be performed to make articular surfaces perpendicular to the mechanical axis for implantation of a prosthetic joint, the collateral ligament at the narrow side has to be pulled open to rectify the so-called genu varum or genu valgum, and this pulled, loosen collateral ligament can cause the implanted knee joint to be stable and lead to after effects such as a weak limb and pains.

Another conventional approach to resection the proximal tibia and the distal femur is the so-call kinematic alignment (KA). The term "kinematic axis" refers to a reference axis upon which the medial/lateral condyle femur pivot against the tibial plateau as the lower limb flexes. This approach is different from the MA-based knee arthroplasty described previously.

Particularly, with use of the kinematic axis for alignment during knee arthroplasty, the rectified articular surfaces of the proximal tibia and the distal femur are almost coincident with the articular surfaces before resection. In other words, the original angles of the tibia and the femur remain unchanged after the surgery, and there is no need to pull the collateral ligaments at two sides of the knee joint, thereby eliminating the after effects as seen in MA-based knee arthroplasty.

The "kinematic axis" is a virtual, imaginary axis, not visible to bared eyes. A known solution to find the kinematic axis is about using image measurement to identify the vertical positions of a patient's femur and tibia, performing computation for modeling based on the dynamics of the patient's swaying lower limb, then establishing a personal specific instrument (PSI), and using the instrument to perform kinematic alignment for knee arthroplasty. However, the process of establishing such a PSI is time-consuming and costly. To be specific, for example, after foregoing image measurement, computation and modeling, the data collected are sent to Singapore for verification before used by a factory in Belgium to make the mold and the instrument. The whole process can take several weeks to a month, and the spending is high, hindering popularization of knee arthroplasty based on kinematic alignment.

For example, U.S. Pat. No. 8,900,242 discloses a stylus assembly, which puts an end (17 or 18) against the posterior femoral condyle (56) to provide reference surface for positioning, and then cutting of the proximal tibia is performed according to the reference surface. The Patented stylus assembly is also based on alignment of the mechanical axis. The existing device may have the end made with different thickness (such as 1-3 mm) to cater for various degrees of abrasion of articular surfaces. In use, the known device works by bracing condyles of a knee joint to tension and restore the loosen medial collateral ligament to its normal tensioned state, but not positioning the kinematic axis. Also, as observed clinically, in the event that the foregoing end is placed to abut against the relatively intact lateral condyle femur and the resulting reference surface is used for resection of the proximal tibia, it is likely that the worn medial condyle tibia is not resected sufficiently. On the contrary, in the event that the foregoing end is placed to abut against the worn medial condyle femur, it is likely that the relatively intact lateral condyle tibia will be resected too much, and thus additional attention has to be paid to repeated trimming before balanced articular surfaces are achieved, making the process challenging and inconvenient.

SUMMARY OF THE INVENTION

To address the foregoing issues, the present invention provides a kinematic-axis locating device for knee arthroplasty.

The kinematic-axis locating device is used to position the kinematic axis before resection of articular surfaces of a patient's proximal tibia and distal femur.

In one embodiment, the present invention provides a kinematic-axis locating device for knee arthroplasty, the kinematic-axis locating device comprising two spoon-shaped arms and a linking piece, the two spoon-shaped arms being at one side of the linking piece together, the two spoon-shaped arms being shaped symmetrically and curved to correspond to curvatures of a patient's medial condyle femur and lateral condyle femur at respective vector sphere surfaces, the two spoon-shaped arms being configured to be placed between the patient's proximal tibia and the distal femur along a sagittal axis, the proximal tibia and the distal femur being such checked by ligaments that the medial condyle and the lateral condyle using their respective curvatures to hold the two spoon-shaped arms at the patient's tibial plateau, the linking piece naturally defining a reference axis when the two spoon-shaped arms are held in position, and the reference axis being roughly parallel to a kinematic axis upon which the medial condyle and the lateral condyle pivot against the tibial plateau, so that the reference axis can be used as a reference for articular surface resection between the proximal tibia and the distal femur.

Thereby, the disclosed kinematic-axis locating device for knee arthroplasty has a simple structure and is easy to manufacture and operate. Before articular surface resection between the proximal tibia and the distal femur, a reference axis simulating a kinematic axis can be obtained to facilitate articular surface resection between the proximal tibia and the distal femur. As proved in clinical experiments, the disclosed device provided results as accurate as those of the known personal specific instrument in articular surface resection between the proximal tibia and the distal femur, yet is easy to operate. As a result, the time and costs traditionally required by computation and validation for modeling can be significantly reduced.

DETAILED DESCRIPTION OF THE INVENTION

The following preferred embodiments when read with the accompanying drawings are made to clearly exhibit the above-mentioned and other technical contents, features and effects of the present invention. Through the exposition by means of the specific embodiments, people would further understand the technical means and effects the present invention adopts to achieve the above-indicated objectives. However, the accompanying drawings are intended for reference and illustration, but not to limit the present invention and are not made to scale.

Referring to FIG. 1 through FIG. 8, the present invention provides a kinematic-axis locating device 100 for knee arthroplasty. As the name suggests, the disclosed device is design to position a kinematic axis during knee arthroplasty. Since the definition of the term "kinematic axis" has been discussed previously, no further details will be provided herein. The kinematic-axis locating device 100 primarily comprises two spoon-shaped arms 10, 20 and a linking piece 30. In a preferred embodiment, it further comprises a guiding member 40.

Figure 1:
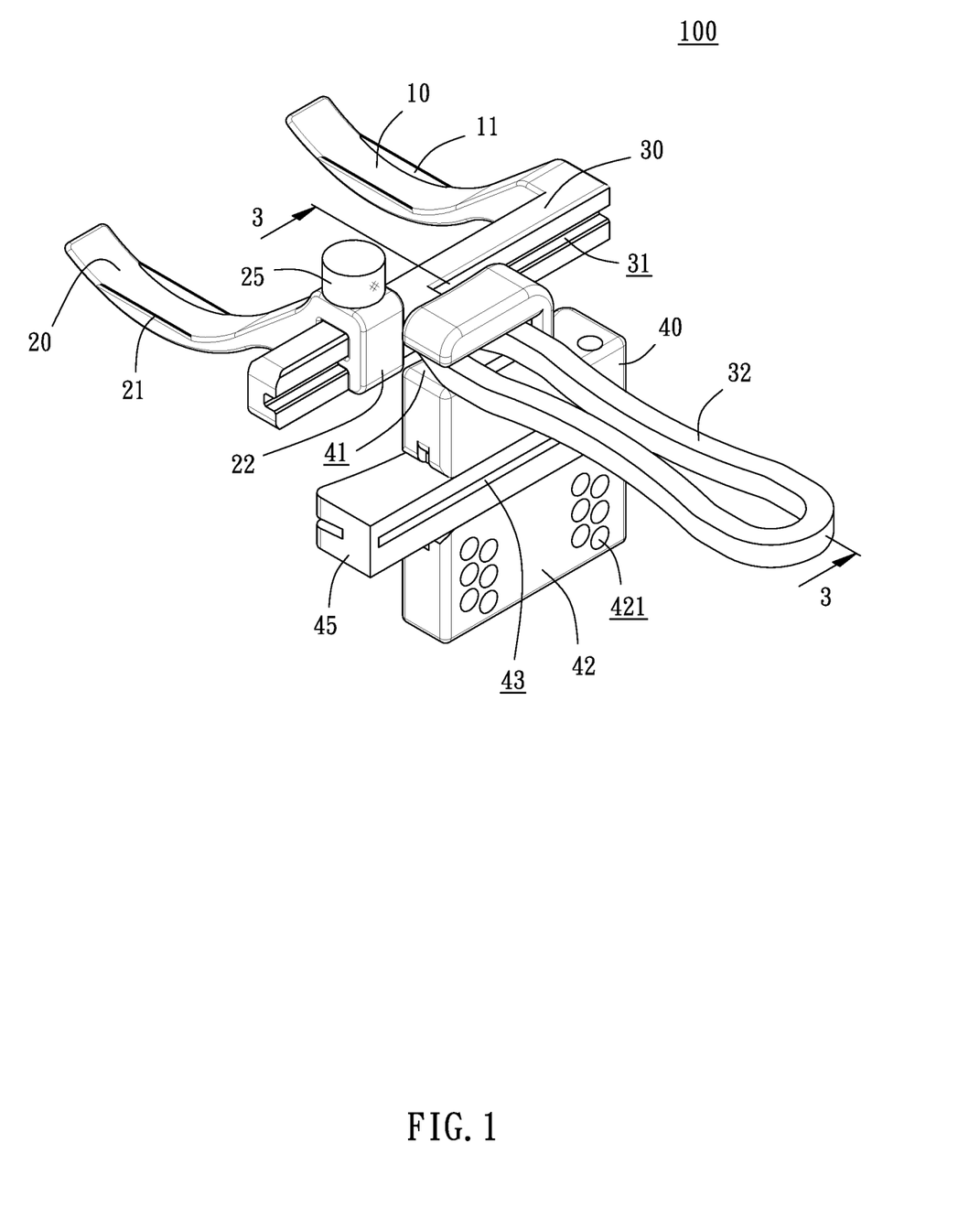
FIG. 1 is a perspective view of a kinematic-axis locating device according to one embodiment of the present invention.
Figure 2:
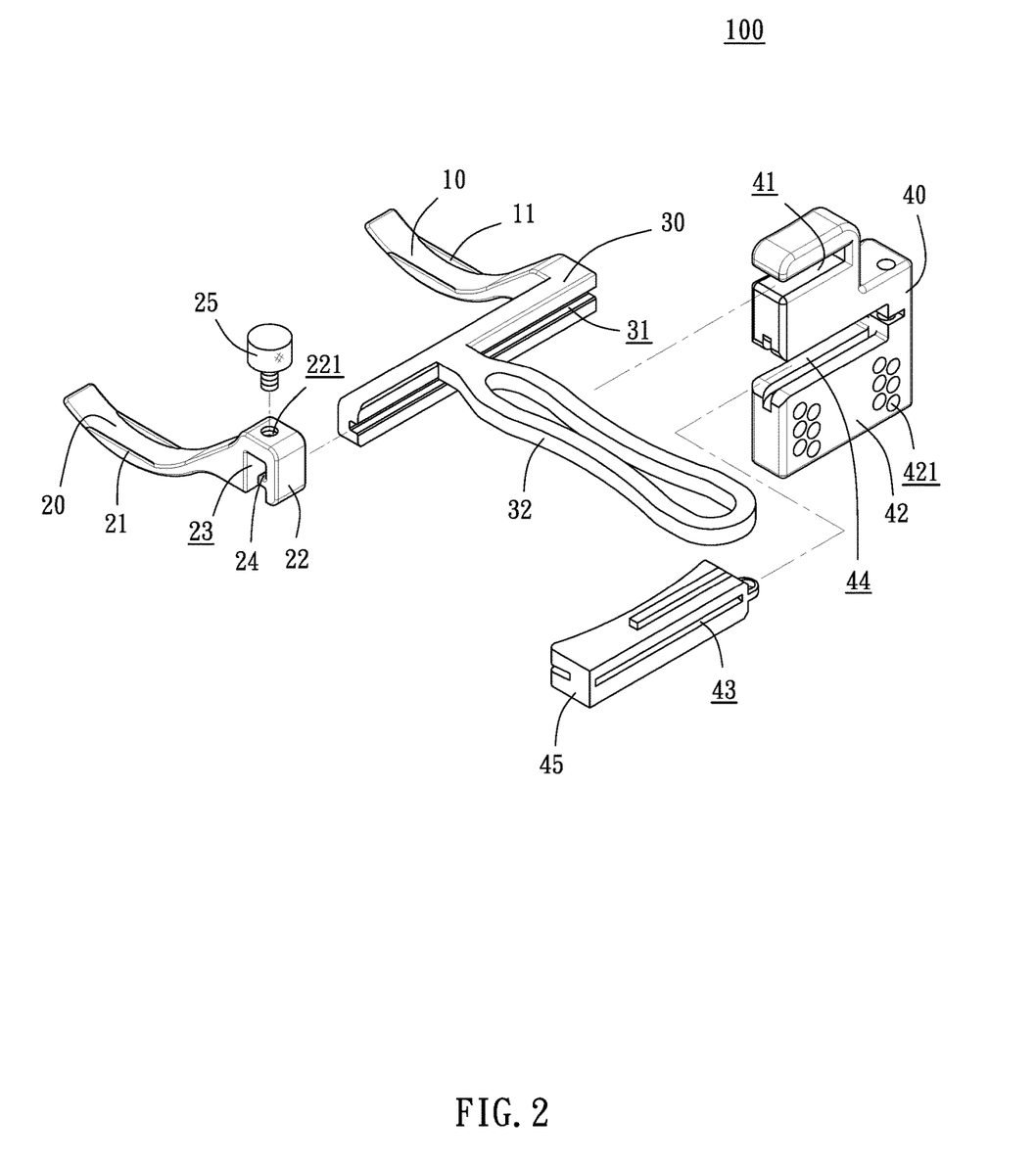
FIG. 2 is an exploded view of the kinematic-axis locating device of FIG. 1.

The two spoon-shaped arms 10, 20 have symmetrical shapes, each curved like a spoon. The curved shapes of the two spoon-shaped arms 10, 20 have a curvature that corresponds to vector sphere surfaces of human medial condyle femur and lateral condyle femur. In the present embodiment, each of the spoon-shaped arms 10, 20 has a flat structure and a smooth surface.

Further, each of the spoon-shaped arms 10, 20 has two lateral walls 11, 21 formed at two edges of its middle part. The two lateral walls 11 of the spoon-shaped arm 10 are symmetrical and the two lateral walls 21 of the spoon-shaped arm 20 are also symmetrical. Each of the laterals wall 11, 21 has a level top.

The linking piece 30 has its one side connected to the two spoon-shaped arms 10, 20. The linking piece 30 in the present embodiment has a lengthwise, linearly extending, rectangular body. The linking piece 30 has two sides opposite to each other in its width direction extending linearly while maintaining parallel to each other.

In the present embodiment, one of the spoon-shaped arms 10 is an immovable spoon-shaped arm, while the other spoon-shaped arm 20 is a movable spoon-shaped arm. The immovable spoon-shaped arm 10 is integratedly formed at one end of the linking piece 30. The spoon-shaped arm 20 is movably attached to the linking piece 30 so that it can slide in the length direction of the linking piece 30 for adjusting the interval between the movable spoon-shaped arm 20 and the immovable spoon-shaped arm 10, after which the spoon-shaped arm 20 can be fixed with respect to the linking piece 30. Preferably, the movable spoon-shaped arm 20 has an end 22 provided with a sliding sleeve 23.

The sliding sleeve 23 has an inner contour slidably fitting the sectional contour of the linking piece 30 so that when the end 22 of the spoon-shaped arm 20 is mounted around the linking piece 30 with the sliding sleeve 23, the spoon-shaped arm 20 is allowed to slide in the length direction of the linking piece 30.

The spoon-shaped arm 20 has a radius of curvature R ranging between 17 mm and 29 mm, in order to be adaptive to various curvatures of the medial condyle femur and the lateral condyle femur against the vector sphere surface, and thereby reflect to the kinematic axis for respective rotation of the medial condyle femur and lateral condyle femur as balls during flexion and extension of the knee joint. In the present embodiment, both of the two spoon-shaped arms 20 have the radius of curvature R of 25 mm. Additionally, in the present embodiment, both of the two spoon-shaped arms 20 have their parts on the vector sphere surface corresponding to the curvature of the medial condyle femur and lateral condyle femur have a thickness t of 1 mm.

Figure 3:
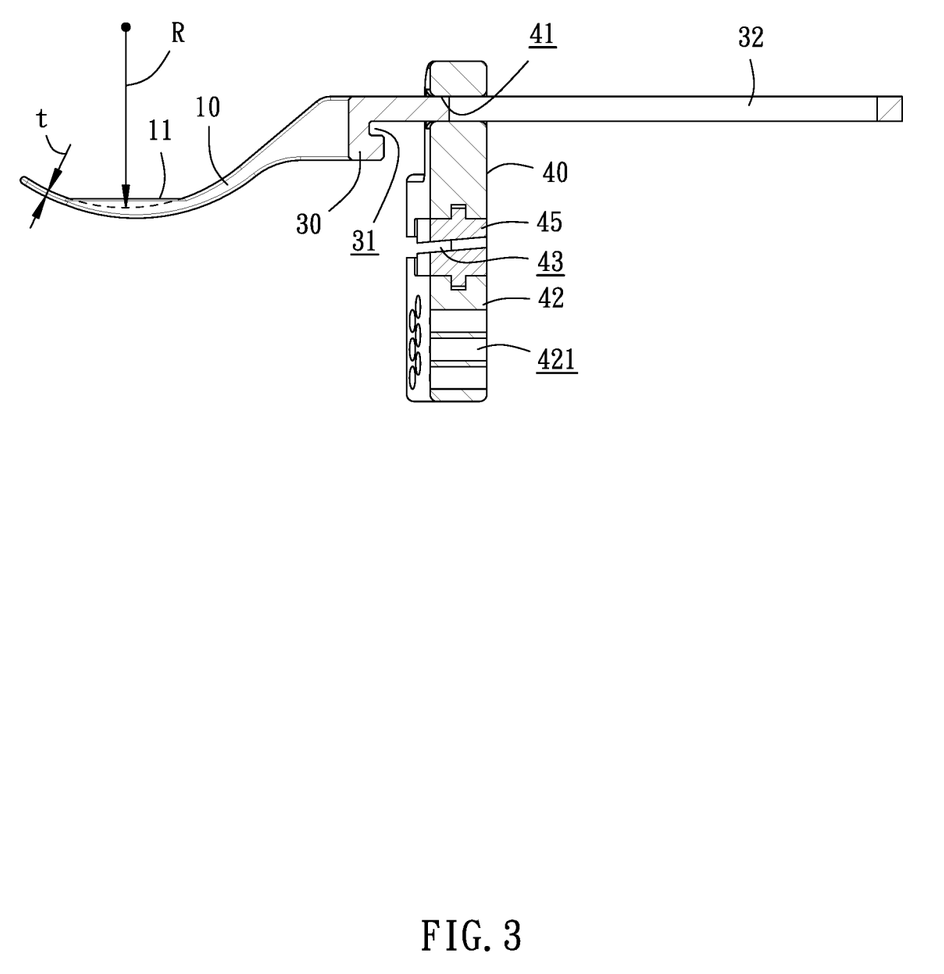
FIG. 3 is a cross-sectional view of the kinematic-axis locating device taken along Line 3-3 of FIG. 1.

Moreover, the linking piece 30 has a guiding groove 31 at its side opposite to the side having the two spoon-shaped arms 10, 20. This guiding groove 31 also extend along the length direction of the linking piece 30 and runs through two ends of the linking piece 30. The end 22 of the spoon-shaped arm 20 has a protuberance 24 formed inside the sliding sleeve. The protuberance 24 is configured to be received in the guiding groove 31. The end 22 further has a pressing member 25 at its side opposite the protuberance 24. When the end 22 is mounted around the linking piece 30 with the sliding sleeve 23 and the protuberance 24 is received in the guiding groove 31, an operator may operate the pressing member 25 to make the pressing member 25 and the protuberance 24 inside the guiding groove 31 jointly hold the linking piece 30 and position the end 22. The combination between the protuberance 24 of the end 22 and the guiding groove 31 of the linking piece 30 merely represents one mode of the present invention. In other embodiments, the protuberance 24 may be alternatively provided on the linking piece 30, and the guiding groove 31 is formed on the end 22 to equivalently limit the slide of the end 22 with respect to the linking piece 30.

Preferably, the pressing member 25 in the present embodiment is a bolt, and the end 22 is provided with a threaded hole 221 corresponding to the pressing member 25. The pressing member 25 as the bolt is configured to be screwed into the threaded hole 221 until it abuts against the linking piece 30. When the pressing member 25 is screwed into the threaded hole 221 at a certain depth, it works with the protuberance 24 to position the end 22 with respect to the linking piece 30, thereby fixing the spoon-shaped arm 20 to the linking piece 30.

Additionally, in the present embodiment, the linking piece 30 has a handle 32, which extends in a direction that is perpendicular to the linearly extending direction of the linking piece 30. In other words, the handle 32 and the linking piece 30 form a T-shaped assembly. The extending direction of the handle 32 is opposite to those of the two spoon-shaped arms 10, 20 against the linking piece 30. In the present embodiment, the handle 32 extends from the side of the linking piece 30 that is provided with the guiding groove 31. The handle 32 is positioned between the two spoon-shaped arms 10, 20 for an operator to easily grasp.

Figure 4:
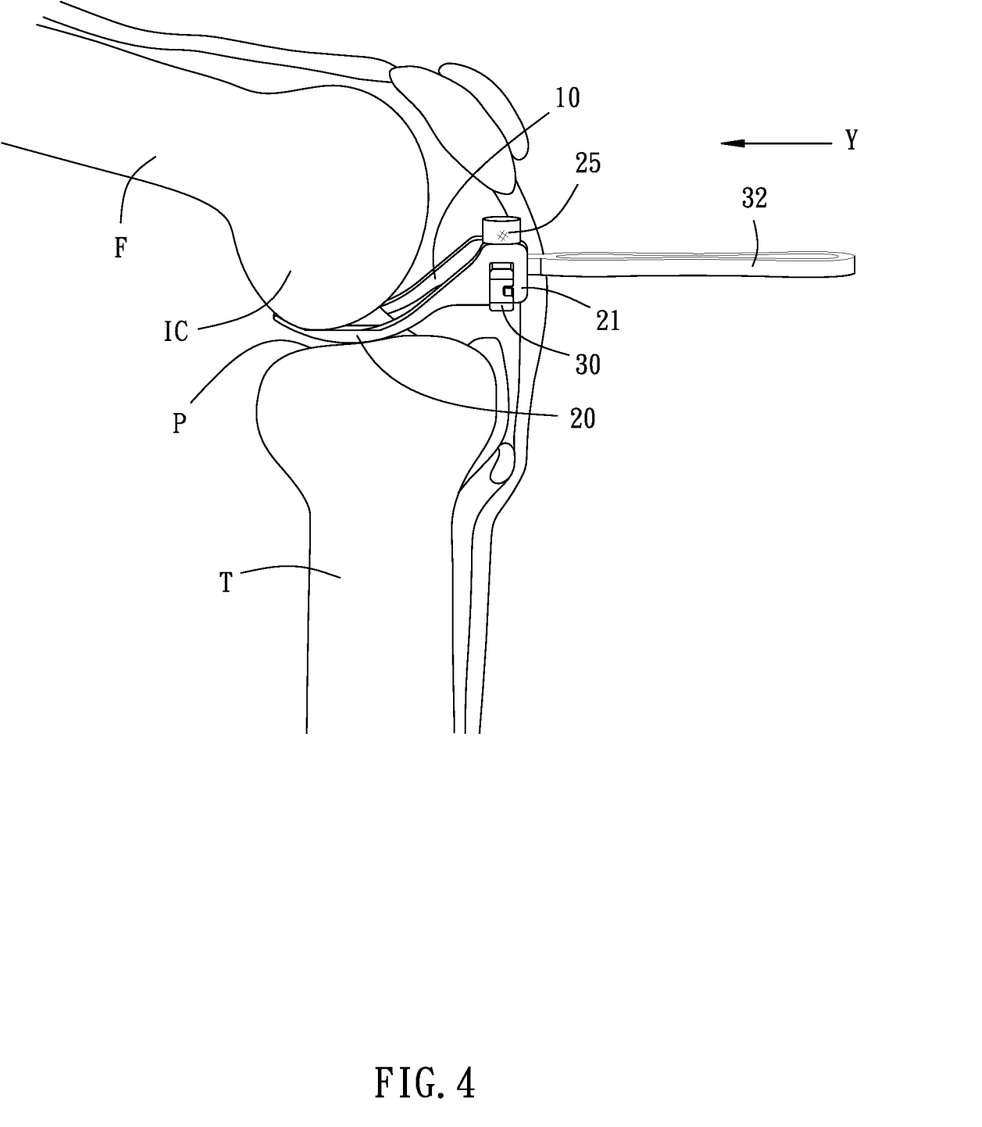
FIG. 4 is a lateral applied view of the kinematic-axis locating device whose two spoon-shaped arms are placed into a knee joint along a sagittal axis.
Figure 5:
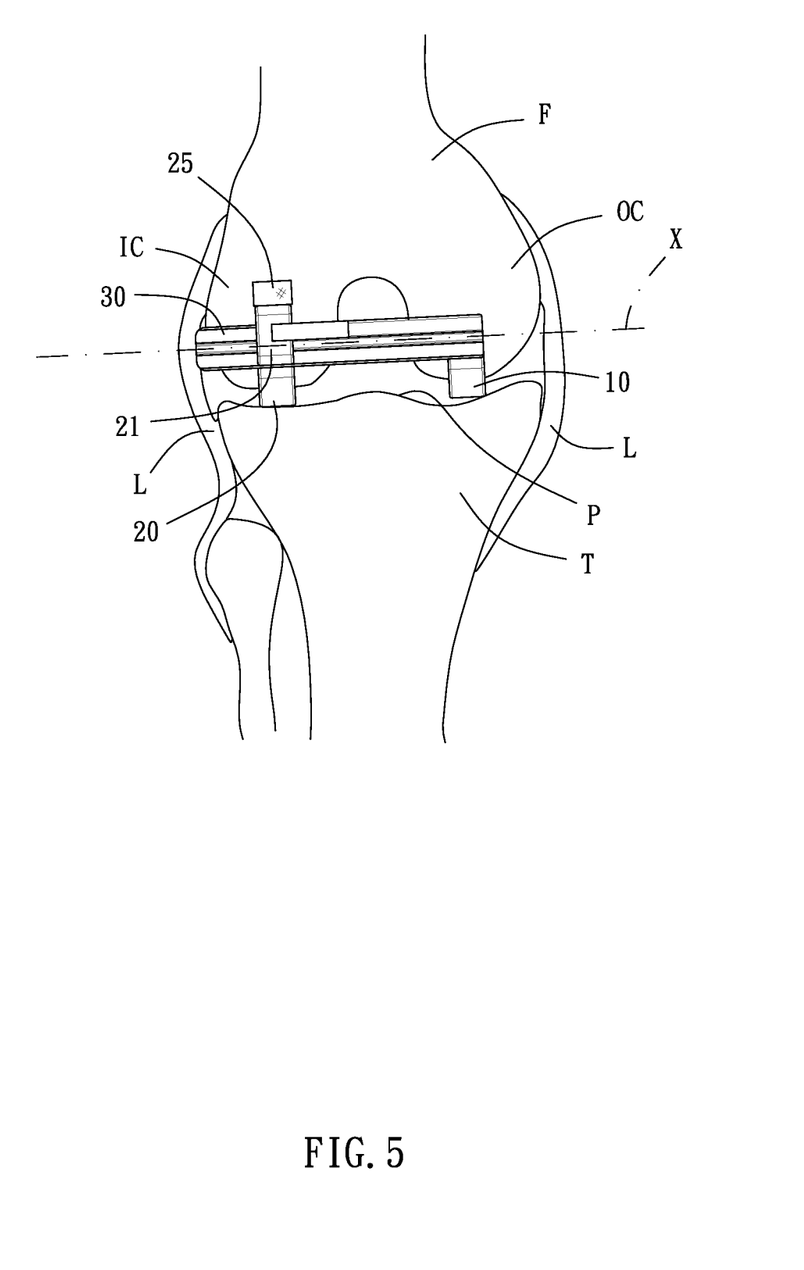
FIG. 5 is a front applied view of the kinematic-axis locating device according to FIG. 4.
Figure 8:
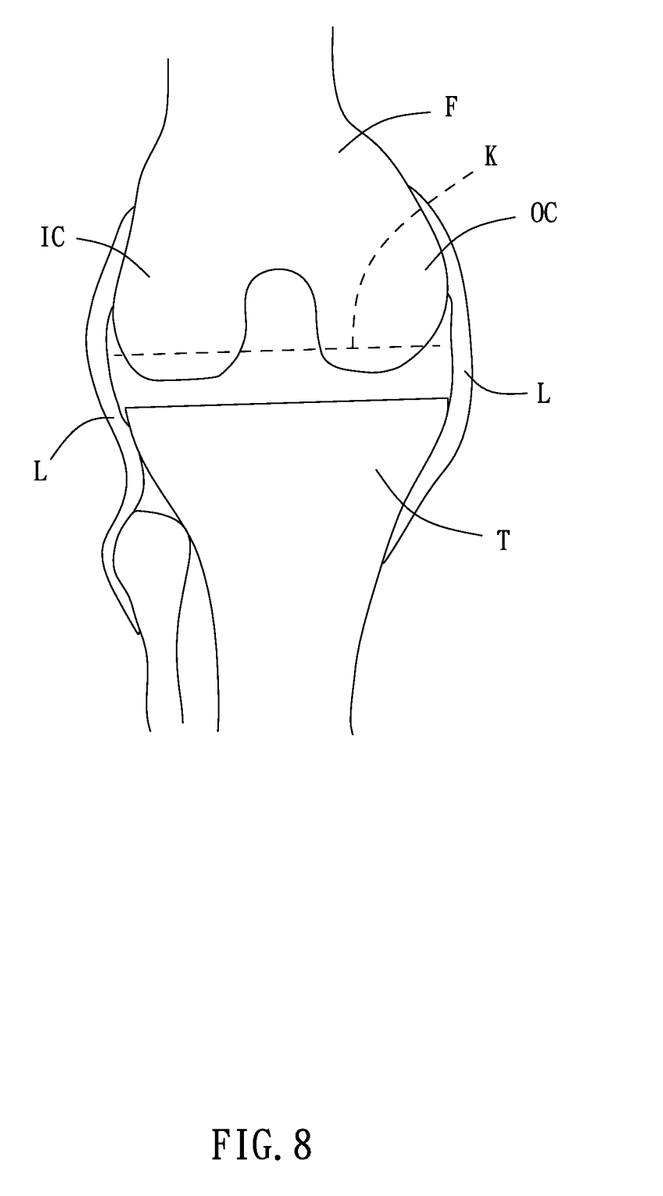
FIG. 8 is a schematic drawing showing the proximal tibia has been corrected by resecting the tibial plateau, wherein the cut of the tibial plateau is parallel to the kinematic axis.

Use of the kinematic-axis locating device 100 of this embodiment will be described blow with reference to a knee replacement surgery performed on, for example, a patient's left leg. In such surgery, the patient's skin and muscular tissues at the knee joint are first cut to expose the proximal tibia T and the distal femur F. Then the two spoon-shaped arms 10, 20 are placed between the proximal tibia T and the distal femur F along the sagittal axis Y (as shown in FIG. 4). At this time, due to the checking effects of the ligaments L (including the lateral collateral ligament and the cruciate ligament) in the proximal tibia T and the distal femur F, the proximal tibia T and the distal femur F maintain opposite pull forces, which make the two spoon-shaped arms 10, 20 keep contacting the tibial plateau P between the medial condyle IC and the lateral condyle OC, and make the medial condyle IC and the lateral condyle OC hold the two spoon-shaped arms 10, 20 at the tibial plateau P using their respective curvatures (as shown in FIG. 5). As the two spoon-shaped arms 10, 20 may be level or have a height distance therebetween in the horizontal parallel, the linking piece 30 provides a reference axis X that is naturally defined by the two inserted and positioned spoon-shaped arms 10, 20. The reference axis X is roughly parallel to the kinematic axis K upon which the medial condyle IC and the lateral condyle OC pivot against the tibial plateau P (as shown in FIG. 8). At this time, articular surface resection of the plateau P between the proximal tibia T and the distal femur F can be performed by following the reference axis X.

Figure 6:
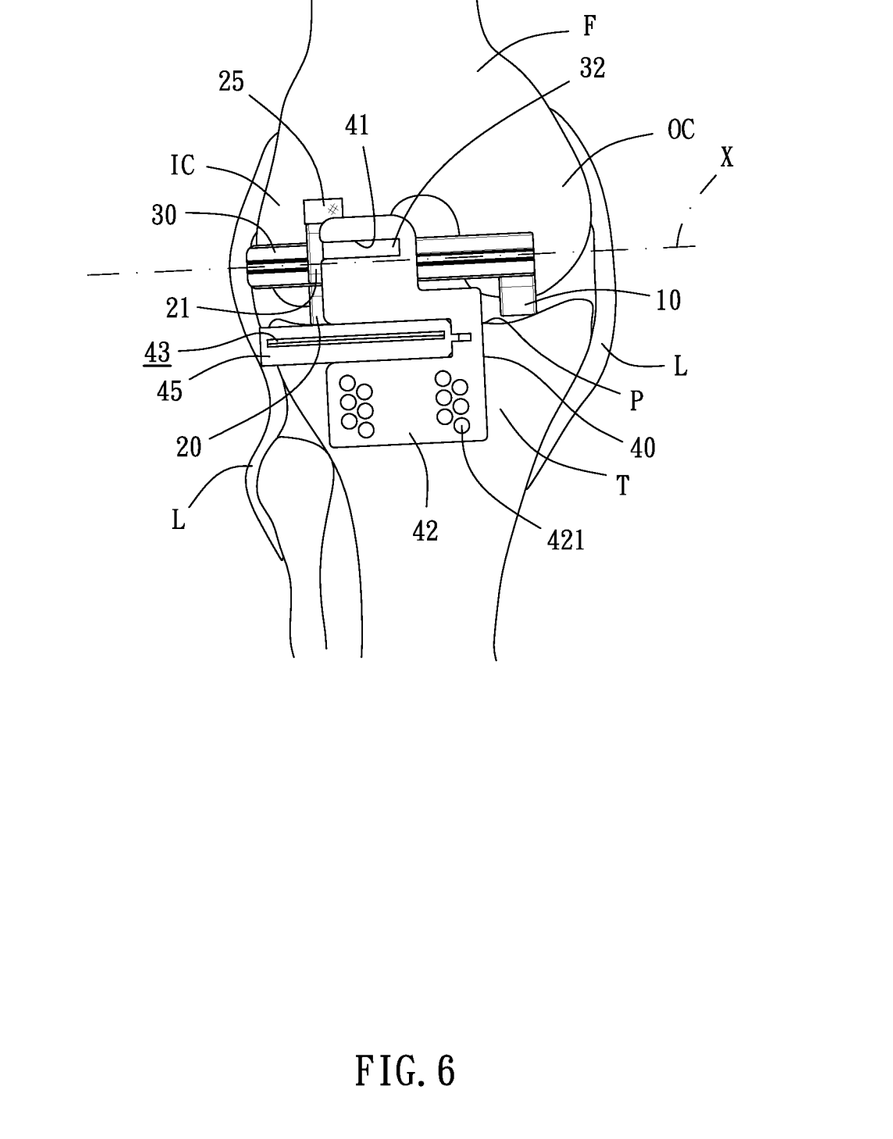
FIG. 6 is a front applied view of the kinematic-axis locating device according to FIG. 5, showing a handle of the kinematic-axis locating device equipped with a guiding member.
Figure 7:
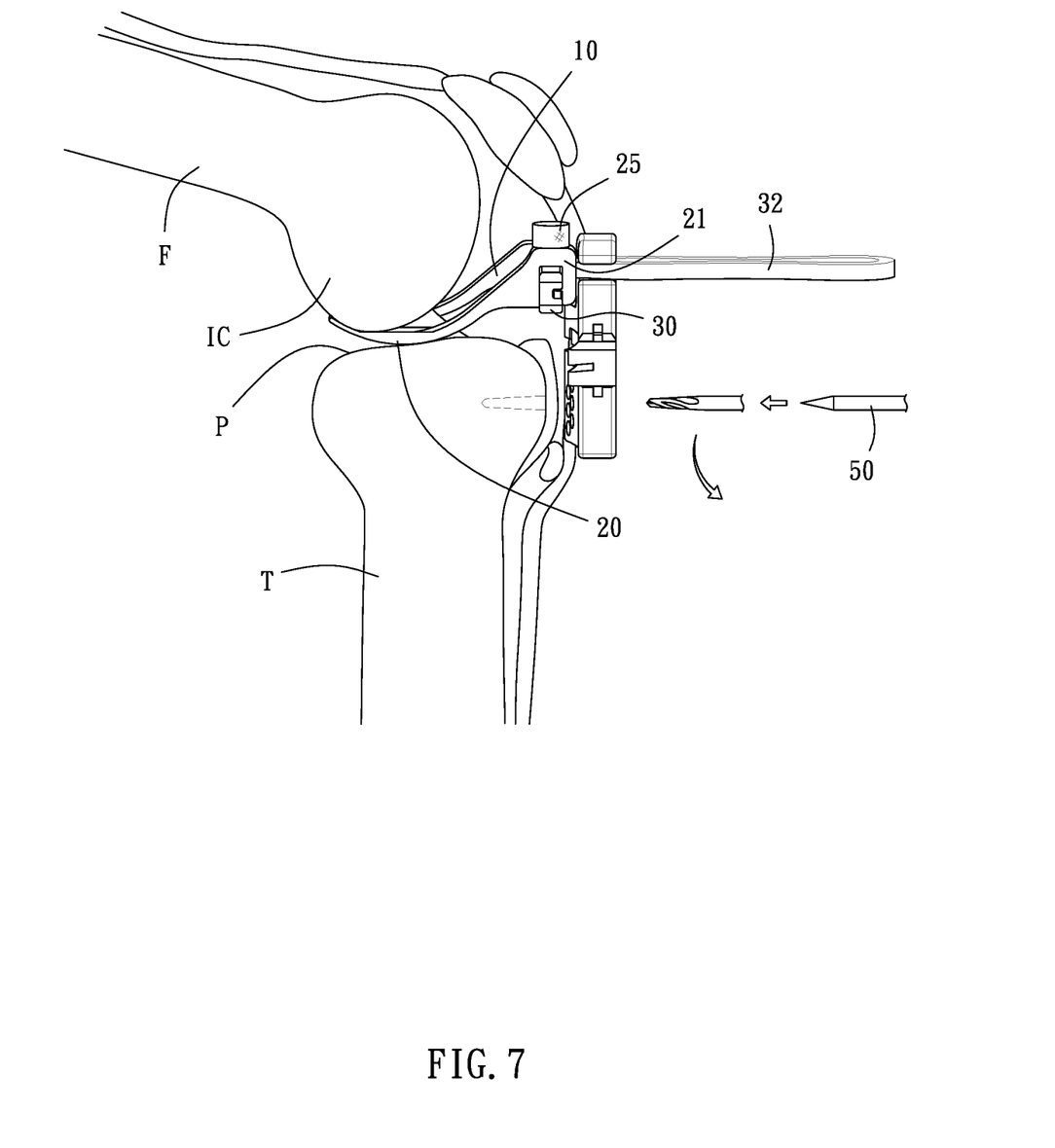
FIG. 7 is an applied view of the kinematic-axis locating device according to FIG. 6, showing that the guiding member is to be fixed to the proximal tibia using bone screws.

In a preferred embodiment of the present invention, the kinematic-axis locating device 100 further comprises a guiding member 40 that is designed to facilitate resection of the plateau P. During knee arthroplasty, after the linking piece 30 defines the reference axis X, the guiding member 40 has a notch 41 and a fastening portion 42. The notch 41 is positionally high on the guiding member 40 while the fastening portion 42 is positionally low on the guiding member 40. The guiding member 40 further has a slot 43 located between the notch 41 and the fastening portion 42.

Preferably, the guiding member 40 has a socket 44 between the notch 41 and the fastening portion 42. The socket 44 is open at one lateral of the guiding member 40. The guiding member 40 has a plug 45 on which the slot 43 is formed. The plug 45 is configured to be fitted into the socket 44 through the open lateral of the guiding member 40 so that the plug 45 is positioned in the socket 44.

Moreover, the fastening portion 42 has a plurality of through holes 421 each for a bone screw 50 to pass therethrough during surgery so that the fastening portion 42 can be fixed to the proximal tibia T at an appropriate site. Furthermore, the slot 43 on the plug 45 is downward inclined from the side of the linking piece 30 having the handle 32 toward the side having the two spoon-shaped arms 10, 20 (as shown in FIG. 3). Since the plug 45 is detachably assembled to the guiding member 40, the slot 43 of the plug 45 may be designed with different slopes.

In practical use, different plugs 45 with slots 43 having different slopes may be selected to work with the guiding member 40 as required by the intended prosthetic joint replacement.

In the same example, as the surgery proceeds, after the two spoon-shaped arms 10, 20 such positioned that the linking piece 30 naturally defines the reference axis X, the handle 32 juts out of the linking piece 30 and exposed. At this time, the guiding member 40 is mounted on the handle 32 with the notch 41 fittingly receiving the thickness of the handle 32 (as shown in FIG. 6). Then the guiding member 40 slides toward the proximal tibia T along the handle 32, after which bone screws 50 passing through relevant through holes 421 are screwed into the proximal tibia T (as shown in FIG. 7), thereby positioning the fastening portion 42 of the guiding member 40 with respect to the proximal tibia T. As a result, the slot 43 on the plug 45 has its length direction parallel to the reference axis X. An osteotome (not shown) can then be put into the slot 43 to resect the tibial plateau P along the reference axis X, thereby achieving articular surface resection between the proximal tibia T and the distal femur F. With the tibial plateau removed, the proximal tibia T has a cut parallel to the kinematic axis K (i.e. the reference axis X).

From the foregoing description it is clear that the present invention has the following advantages. First, the disclosed kinematic-axis locating device 100 for knee arthroplasty has a simple structure that is only composed of two spoon-shaped arms 10, 20 and a linking piece 30, making it easy to manufacture and operate. Second, before articular surface resection between the proximal tibia and the distal femur, with the medial condyle IC and the lateral condyle OC using their respective curvatures to hold the two spoon-shaped arms 10, 20 at the tibial plateau P, a reference axis X simulating the kinematic axis can be obtained to facilitate such resection. As proved in clinical experiments, the disclosed device provided results as accurate as those of the known personal specific instrument in articular surface resection between the proximal tibia and the distal femur and achieved a balanced state rapidly without the need of repeated correction during surgery. This means even a relatively less experienced surgeon can easily and successfully perform the operation with the help of the reference axis X provided by the disclosed kinematic-axis locating device 100. As a result, the time and costs traditionally required by computation and validation for modeling can be significantly reduced.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A kinematic-axis locating device for knee arthroplasty, the kinematic-axis locating device comprising two spoon-shaped arms and a linking piece, the two spoon-shaped arms being at one side of the linking piece together, the two spoon-shaped arms being shaped symmetrically and curved to correspond to curvatures of a patient's medial condyle femur and lateral condyle femur at respective vector sphere surfaces, the two spoon-shaped arms being configured to be placed between the patient's proximal tibia and the distal femur along a sagittal axis, the proximal tibia and the distal femur being such checked by ligaments that the medial condyle and the lateral condyle using their respective curvatures to hold the two spoon-shaped arms at the patient's tibial plateau, the linking piece naturally defining a reference axis when the two spoon-shaped arms are held in position, and the reference axis being roughly parallel to a kinematic axis upon which the medial condyle and the lateral condyle pivot against the tibial plateau, so that the reference axis can be used as a reference for articular surface resection between the proximal tibia and the distal femur;
wherein the linking piece has a lengthwise, linearly extending, rectangular body, and the two spoon-shaped arms include an immovable spoon-shaped arm that is integratedly formed at one end of the linking piece and a movable spoon-shaped arm that is movably attached to the linking piece so as to slide in a length direction of the linking piece for adjusting an interval between the movable spoon-shaped arm and the immovable spoon-shaped arm and then being fixed to the linking piece; and
wherein the movable spoon-shaped arm has an end provided with a sliding sleeve, the sliding sleeve having an inner contour corresponding to a sectional contour of the linking piece, and the end being configured to be such mounted around the linking piece that the sliding sleeve is allowed to slide along the length direction.

2. The kinematic-axis locating device for knee arthroplasty of claim 1, wherein the linking piece has a guiding groove at its side opposite to the two spoon-shaped arms, the guiding groove extending along the length direction of the linking piece, the end having a protuberance formed inside the sliding sleeve and corresponding to the guiding groove, and the end having its side opposite to the protuberance provided with a pressing member, so that when the end has the sliding sleeve mounted around the linking piece and the protuberance is received in the guiding groove, the pressing member can be operated to work with the protuberance to hold the linking piece and position the end.

3. The kinematic-axis locating device for knee arthroplasty of claim 2, wherein the pressing member is a bolt, and the end has a threaded hole corresponding to the pressing member, in which the pressing member is configured to be screwed into the threaded hole until abutting against the linking piece and working with the protuberance to hold the end on the linking piece.

4. The kinematic-axis locating device for knee arthroplasty of claim 1, wherein the linking piece has a handle, which extends in an extending direction that is perpendicular to the length direction of the linking piece and opposite to an extending direction of the two spoon-shaped arms away from the linking piece, the handle being located between the two spoon-shaped arms, and wherein the two spoon-shaped arms each have a radius of curvature ranging between 17 mm and 29 mm.

5. The kinematic-axis locating device for knee arthroplasty of claim 4, further comprising a guiding member that has a notch located positionally high and a fastening portion located positionally low, and has a slot formed between the notch and the fastening portion, so that after the linking piece naturally defines the reference axis, when the handle is fittingly received in the notch, and the fastening portion is configured to be fixed to the proximal tibia, the slot has its length direction parallel the reference axis for an osteotome to be put therein and used to resect the tibial plateau along the reference axis.

6. The kinematic-axis locating device for knee arthroplasty of claim 5, wherein the guiding member has a socket located between the notch and the fastening portion, in which the socket is open at one lateral of the guiding member and the guiding member has a plug that is provided with the slot, so that the plug can be received and positioned by the socket through the open lateral.

7. The kinematic-axis locating device for knee arthroplasty of claim 6, wherein the slot is downward inclined from the side of the linking piece having the handle toward the side of the linking piece having the two spoon-shaped arms in a width direction of the plug.

8. The kinematic-axis locating device for knee arthroplasty of claim 5, wherein the fastening portion has a plurality of through holes, each for a bone screw to pass therethrough during surgery so that the fastening portion can be fixed to the proximal tibia at an appropriate site.

* * * * *